(12) United States Patent
Pfenniger et al.

(10) Patent No.: US 8,075,516 B2
(45) Date of Patent: Dec. 13, 2011

(54) PORTABLE BREASTPUMP

(75) Inventors: Erich Pfenniger, Ebikon (CH); Richard Röllin, Menzingen (CH); Beda Weber, Sins (CH); Markus Kerschdorfer, Neuheim (CH)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 12/707,555

(22) Filed: Feb. 17, 2010

(65) Prior Publication Data

US 2010/0145264 A1 Jun. 10, 2010

Related U.S. Application Data

(63) Continuation of application No. 11/593,728, filed on Nov. 7, 2006, now abandoned, which is a continuation-in-part of application No. 10/403,824, filed on Mar. 31, 2003, now abandoned.

(30) Foreign Application Priority Data

Feb. 10, 2003 (CH) ...................................... 0197/03

(51) Int. Cl.
*A61M 1/06* (2006.01)

(52) U.S. Cl. .............. 604/73; 206/480; 604/74; 604/75; 604/76; 119/14.1; 119/14.4; 119/14.43

(58) Field of Classification Search ................ 119/14.1, 119/14.4–14.43; 206/480; 604/73–76

See application file for complete search history.

(56) References Cited

U.S. PATENT DOCUMENTS

| 2,029,521 | A | * | 2/1936 | Couch | 384/190.2 |
|---|---|---|---|---|---|
| 2,207,047 | A | * | 7/1940 | Buckius | 384/190.2 |
| 3,851,783 | A | * | 12/1974 | Braginetz | 215/232 |
| 3,946,498 | A | * | 3/1976 | Waters et al. | 34/99 |
| 3,990,598 | A | * | 11/1976 | Zapp et al. | 215/272 |
| 4,607,596 | A | * | 8/1986 | Whittlestone et al. | 119/14.02 |
| 4,673,388 | A | * | 6/1987 | Schlensog et al. | 604/74 |
| 4,794,915 | A | * | 1/1989 | Larsson | 601/153 |
| 4,961,726 | A | * | 10/1990 | Richter | 604/74 |
| 5,007,899 | A | * | 4/1991 | Larsson | 604/74 |
| 5,304,129 | A | * | 4/1994 | Forgach | 604/74 |
| 5,330,431 | A | * | 7/1994 | Herskowitz | 604/153 |
| 5,571,084 | A | * | 11/1996 | Palmer | 604/74 |
| 5,598,926 | A | * | 2/1997 | Vogt | 206/457 |
| 5,616,125 | A | * | 4/1997 | Jelks | 604/74 |
| 5,639,004 | A | * | 6/1997 | Carlton et al. | 224/579 |
| 5,776,098 | A | * | 7/1998 | Silver et al. | 604/74 |
| 6,004,186 | A | * | 12/1999 | Penny | 450/36 |

(Continued)

FOREIGN PATENT DOCUMENTS

WO WO 9641570 A1 * 12/1996

*Primary Examiner* — Jackie Ho
*Assistant Examiner* — Scott Medway
(74) *Attorney, Agent, or Firm* — McDonnell Boehnen Hulbert & Berghoff LLP

(57) ABSTRACT

A portable breast pump has a suction unit and a collecting unit which is connected to this suction unit via a flexible suction line. The collecting unit comprises a breast shield, a milk-receiving container and a coupling element which connects the breast shield to the milk-receiving container. The suction unit has a housing with an operating means for operating the pump and a fastening means for fastening the housing on a carrying means, which can be fastened on the mother's body. This breast pump is easy to operate, allows the milk to be expressed even in confined areas with no set-down surfaces and, in addition, does not hinder the mother's mobility.

11 Claims, 2 Drawing Sheets

U.S. PATENT DOCUMENTS

| | | | |
|---|---|---|---|
| 6,123,240 A * | 9/2000 | Fowles et al. | 224/600 |
| 6,139,521 A * | 10/2000 | Larsson | 604/74 |
| 6,257,847 B1 * | 7/2001 | Silver et al. | 417/415 |
| 6,379,327 B2 * | 4/2002 | Lundy | 604/74 |
| 6,383,163 B1 * | 5/2002 | Kelly et al. | 604/74 |
| 6,440,100 B1 * | 8/2002 | Prentiss | 604/74 |
| 6,702,167 B2 * | 3/2004 | Annis | 224/576 |
| 6,749,582 B2 * | 6/2004 | Britto et al. | 604/74 |
| 7,201,735 B2 * | 4/2007 | Atkin et al. | 604/74 |
| 7,223,255 B2 * | 5/2007 | Myers et al. | 604/74 |
| 7,236,751 B2 * | 6/2007 | Ono | 455/90.3 |
| 7,559,915 B2 * | 7/2009 | Dao et al. | 604/74 |
| 7,611,399 B2 * | 11/2009 | Brigham | 450/36 |
| 7,824,363 B2 * | 11/2010 | Myers | 604/74 |
| 7,833,190 B1 * | 11/2010 | Hall | 604/74 |
| 2001/0047148 A1 * | 11/2001 | Suh | 604/74 |
| 2002/0193731 A1 * | 12/2002 | Myers et al. | 604/74 |
| 2003/0139702 A1 | 7/2003 | Renz et al. | |
| 2005/0038315 A1 * | 2/2005 | Eckstein et al. | 600/35 |

* cited by examiner

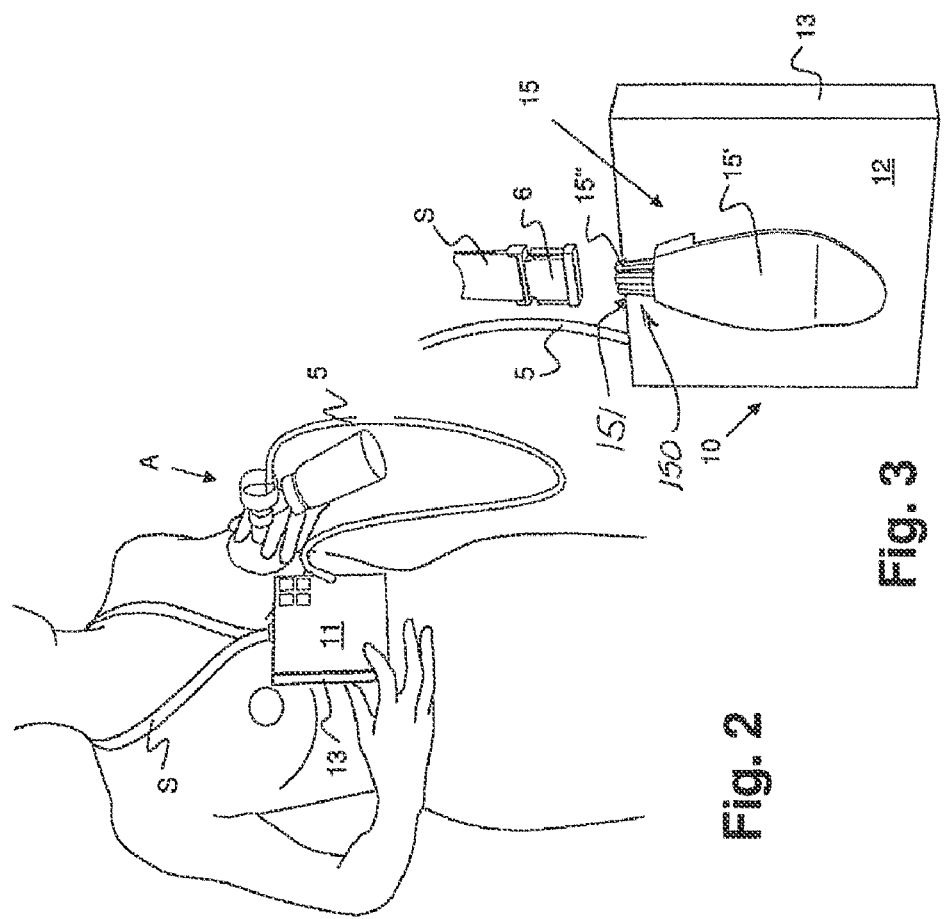
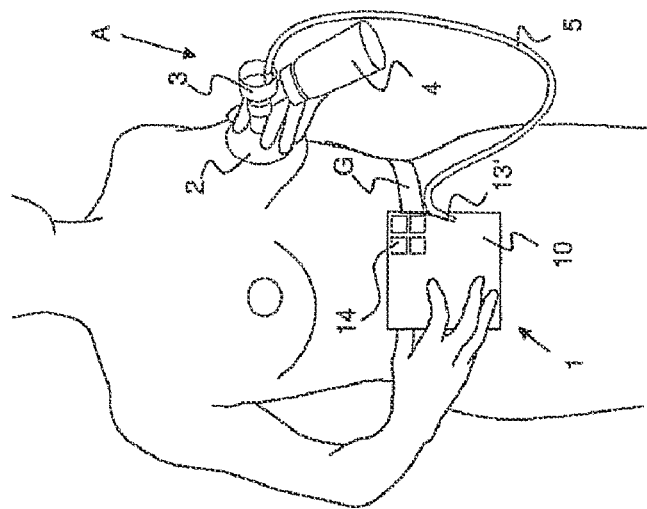
Fig. 1
Fig. 2
Fig. 3

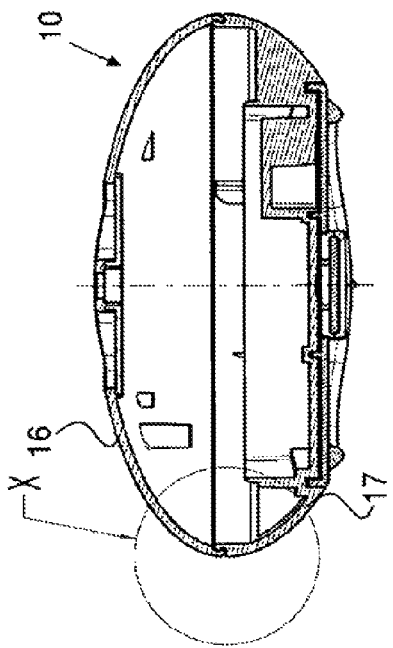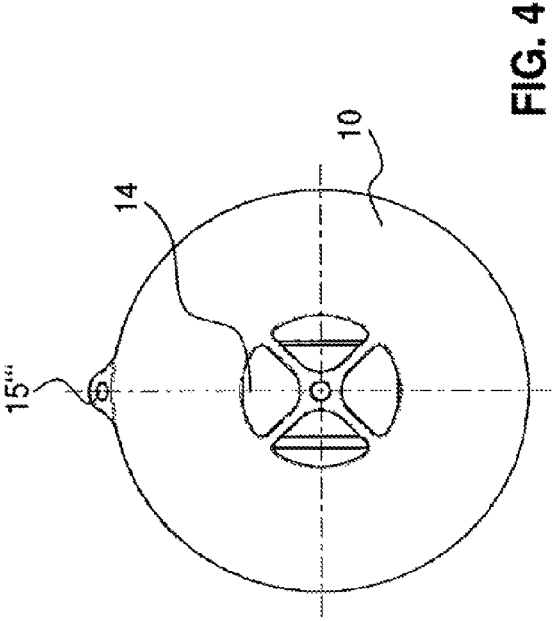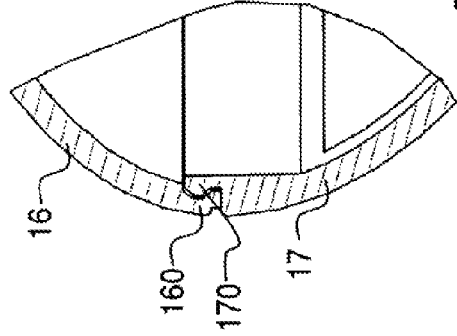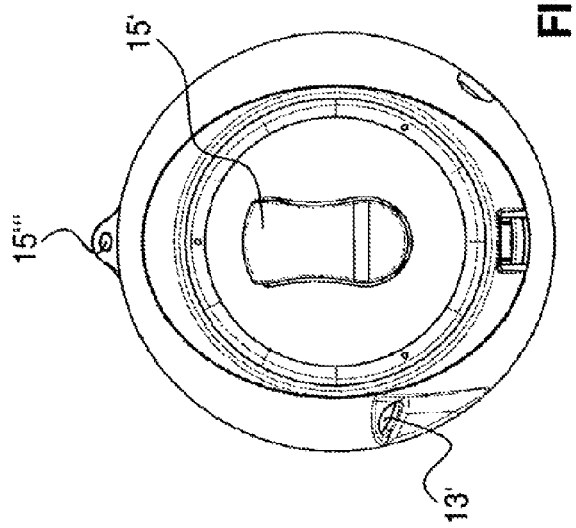

PORTABLE BREASTPUMP

CROSS REFERENCE TO RELATED APPLICATIONS

This application is a continuation of U.S. patent application Ser. No. 11/593,728 filed Nov. 7, 2006 which is a continuation-in-part of U.S. patent application Ser. No. 10/403,824 filed Mar. 31, 2003 which claims benefit from Switzerland Patent Application No. 2003 0197/03 filed Feb. 10, 2003, the specifications of each of which are incorporated by reference herein.

FIELD OF THE INVENTION

The invention relates to a portable breast pump and to a suction unit for use with this portable breast pump.

BACKGROUND OF THE INVENTION

Portable breast pumps are known. They have the advantage that a mother can carry them along everywhere and thus maintain a certain degree of independence even throughout the months she is breast-feeding. It is not always easy, however, to find a suitable area in which the mother can express the milk without being disturbed. Working mothers in particular often have to do this in the ladies' toilets in the workplace. In such areas, however, it is usually difficult to find a suitable set-down surface for the breast pump.

U.S. Pat. No. 6,379,327 discloses a breast-pump system in the case of which the mother can carry all the elements of the breast pump on her body. This system comprises a bra with an integrated breast shield and a wide band which is worn around the stomach and has a first pocket for accommodating a suction unit and a second pocket for accommodating a milk-receiving container. The suction unit and the milk-receiving container are connected to the breast shield, in each case via a dedicated line. The entire system is worn beneath the clothing. This has the disadvantage that the mother always has to carry the breast pump around with her, which is regarded as being awkward and hinders the mother in doing anything else. In addition, the suction unit is of a not inconsiderable weight, with the result that the mother will not really want to carry it for a long period of time. Furthermore, the operating buttons of the breast pump are likewise concealed beneath the clothing and are thus not easily accessible.

A similar breast pump is also disclosed in U.S. Pat. No. 6,440,100, the arrangement of the suction unit not being explained specifically here.

GB-A-2,366,732 describes a portable breast pump which is carried over the shoulder on a support, the support being length-adjustable. The suction unit is arranged at the bottom front end of the support. The breast attachment cap and the milk-receiving container are fastened on the suction unit by a coupling part. This system can indeed be worn above the clothing, and thus need only be attached as required. The disadvantage, however, is that it is of relatively rigid design, with the result that the mother is hardly able to move as the milk is being expressed. In addition, the suction unit has to be of relatively small design in order that the support does not protrude too far. Small suction units, however, usually also have a low suction capacity and/or have only a rudimentary control means.

SUMMARY OF THE INVENTION

It is an object of the invention to provide a portable breast pump which eliminates the abovementioned disadvantages.

This object is achieved by a portable breast pump comprising: a suction unit, a collecting unit and a suction line, the suction line connecting the collecting unit to the suction unit, the collecting unit having a breast shield, a milk-receiving container and a coupling element, which connects the breast shield to the milk-receiving container to form a rigid unit, and the suction unit having a housing, wherein the housing is provided with a fastening means for fastening the housing on a carrying means, which can be fastened on a mother's body so that the suction unit can be carried in an exposed manner, wherein the housing has a round cross-section and comprises an upper part and a lower part, wherein the upper part and the lower part are connected with each other by a circulating ball spring-actuated lock.

This object is further achieved by a a suction unit for use in a portable breast pump comprising; a breast pump having a collecting unit with a breast shield, a milk-receiving container and a coupling element, which connects the breast shield to the milk-receiving container for form a rigid unit, the breast pump also having a flexible suction line, by means of which the collecting unit can be connected to the suction unit, and the suction unit having a housing, wherein the housing is provided with a fastening means for fastening the housing on a carrying means, which can be fastened on a mother's body so that the suction unit can be carried in an exposed manner, wherein the housing has a round cross-section and comprises an upper part and a lower part, wherein the upper part and the lower part are connected with each other by a circulating ball spring-actuated lock.

This object is also achieved by a portable breast pump comprising: a suction unit, a collecting unit and a suction line, the suction line connecting the collecting unit to the suction unit, the collecting unit having a breast shield, a milk-receiving container and a coupling element, which connects the breast shield to the milk-receiving container to form a rigid unit, and the suction unit having a housing, wherein the housing is provided with a fastening means for fastening the housing on a carrying means, which can be fastened on a mother's body so that the suction unit can be carried in an exposed manner, wherein the housing has a round cross-section and comprises an upper part and a lower part, and wherein the fastening means comprises an eye attached to a periphery of the housing, either to the upper part or the lower part.

The connection between the carrying element and fastening means is preferably releasable. It is preferably possible for the housing to be fastened on the mother's trouser or dress belt or to be carried on a loop around the neck.

This breast pump with its suction unit allows the mother to move freely even as the milk is being expressed. In addition, the mother can select the location and how she wishes to carry the suction unit.

If the housing is of flat design, it is more comfortable for the mother to carry. In addition, this prevents the mother from catching herself anywhere on the housing. It is advantageous, furthermore, that the housing may be configured relatively freely in terms of shape, with the result that it can be carried as a fashion accessory without being recognizable at first glance as the suction unit of a breast pump. In addition, the suction unit may be of sufficiently large design to accommodate a sufficiently large electric storage cell and the desired electronics.

Since the suction unit is carried in an exposed manner, any possible operating buttons are easily accessible. In order to increase the accessibility yet further, they are preferably arranged in a front side of the housing.

Further advantageous embodiments can be gathered from the dependent patent claims.

BRIEF DESCRIPTION OF THE DRAWINGS

The subject matter of the invention is explained hereinbelow with reference to preferred exemplary embodiments which are illustrated in the attached drawing, in which:

FIG. 1 shows a portable breast pump according to a first embodiment of the invention with a suction unit, in a first carrying variant;

FIG. 2 shows a breast pump according to FIG. 1 in a second carrying variant;

FIG. 3 shows the suction unit according to FIG. 1 in a view from behind;

FIG. 4 shows a top view of a portable breast pump according to a second embodiment of the invention;

FIG. 5 shows the breast pump of FIG. 4 in a bottom view;

FIG. 6 shows the breast pump of FIG. 4 in a cross sectional view; and

FIG. 7 shows an enlarged view of a detail of FIG. 6.

DETAILED DESCRIPTION

FIG. 1 illustrates a portable breast pump according to the invention. The breast pump has a collecting unit A and a suction unit 1 which is connected thereto via a suction line 5. The suction line 5 is usually a flexible plastic tube.

In this preferred example, the collecting unit A comprises a breast shield 2, a coupling element 3 and a milk-receiving container 4. The coupling element 3 connects the breast shield 2 to the milk-receiving container 4 to form a rigid unit which can be attached to the mother's breast and can be held in the hand as the milk is being expressed. However, it is also possible for the connection between the milk-receiving container 4 and breast shield 2 to be a flexible configuration and for these to be connected to one another by means of a further connecting tube. It is thus possible for the breast shield 2 to be retained on the breast or integrated in a bra. In this variant, the container 4 may be provided with a fastening means in order to attach it, for example, to a belt. It is also possible, however, for it to be held in one hand or positioned on a set-down surface. The embodiment with the rigid unit, however, is the preferred solution in respect of mobility and handling.

The suction unit 1 comprises the elements, which are known in the prior art, for producing a negative pressure in the breast shield 2 which is sufficient for expressing the milk. These elements comprise a suction pump (not illustrated), control electronics and an electric storage element, for example a battery. All of these elements are arranged in a common housing 10. This preferably consists of plastic and is of rigid design. Either it has connection openings for a plug-in connection for connection to an electric charging device for the storage element or it may be opened at least in the region of the battery, in order for the battery to be exchanged.

The housing 10 is preferably of flat design, with a front side 11, a rear side 12 and a lateral surface 13 which connects the two sides. The cross section of the housing 10 may be selected as desired. It may be, in particular, of round, oval or polygonal design. A recess 13' is preferably provided on the housing 10, for example in the lateral surface 13, for the purpose of accommodating one end of the suction line 5. This suction line 5 can preferably be plugged in a releasable manner into this recess 13'.

At least one operating means 14 for actuating the suction pump is provided on the housing 10. In this example, this means is constituted by buttons which are incorporated in the front side 11 of the housing 10.

A fastening means 15, furthermore, is arranged on the housing 10, in order to fasten the housing 10 on a carrying element. In this example, the carrying element is a belt G. The fastening means 15 is preferably arranged on that side of the housing 10 which is located opposite the operating means 14, so in this case on the rear side 12, as can be seen in FIG. 3. In this example, the fastening means 15 comprises a resilient clip 15', in particular made of metal or plastic, and a plug-in closure part 15", in this case made of plug-in pins 150 which are provided, in part, with retaining hooks 151. It is also possible, however, for the housing 10 to be provided just with the clip 15' or just with the plug-in closure part 15". In addition, it is possible to use other known fastening means, for example a touch-and-close fastener.

The suction unit 1 according to the invention can easily be hooked onto a belt G by means of the clip 15'. This belt need not be as special belt, but, rather, may be any belt selected individually by the mother.

In the embodiment according to FIG. 2, the suction unit 1 is carried by way of a loop S around the neck. The loop S may be firmly connected to the housing 10, but it is preferable to select a releasable connection. For example, the bottom end of the loop S may be provided with an associated plug-in closure part 6 for connection to the plug-in closure part 15", as is illustrated in FIG. 3.

It is also possible, however, for the suction unit 1 to be carried in other ways, for example on the arm or hung over the shoulder.

FIGS. 4 to 7 show a breast pump with a round cross section of the housing 10. The operating means 14 are preferably arranged in the centre of the circle described by the housing 10, as best can be seen in FIG. 4. Preferably there are two fastening means, a resilient clip 15' (see FIG. 6) and an eye or loop 15''' on the periphery of the housing 10. The eye 15''' is either attached to the upper or lower part 16, 17 of the housing 10. The eye 15''' enables the mother to carry the pump on a string or ribbon S around the neck. In FIG. 6, the recess 13' for accommodating one end of the suction line 5 can be seen as well.

The cross-sections shown in FIGS. 6 and 7 disclose that the housing 10 comprises an upper part 16 and a lower part 17. The two parts 16, 17 are connected with each other by a snap lock, in more detail by a ball spring-actuated lock. The upper part 16 comprises a recess or groove 160 formed on or in its inner peripheral face and the lower part 17 comprises a ball-shaped nose or bead 170 formed thereon which fits cooperatively into the recess 160. The recess 160 may be formed in a circulating manner about the inner periphery or circumference of the upper part 16. The nose 170 may be formed in a circulating manner about the outer periphery or circumference of the lower part 17. It will be understood that the arrangement of the recess 160 and the nose 170 can also be vice versa, i.e. the recess being arranged or formed in the lower part 17 and the nose arranged or formed in the upper part 16.

The upper and the lower part 16, 17 are both made of stiff material but the walls are so thin that the parts have a small amount of flexibility. Since the housing 10 has a round cross-section, the ball spring-actuated lock can be opened and closed by pressing the wall of the upper or lower part. This lock is sufficiently water tight for the purposes of a breast pump. No screws are needed to fix the parts together and no sealing ring is needed to seal the fitting. The closure can easily be opened by a skilled person but will not be opened by the mother since she can not see an opener.

The round shape of the housing has several advantages: The housing has no edges and there is therefore no risk to hurt oneself at such an edge or to pump the edge into something harder and therefore to damage the pump housing. Only the round shape enables the use of the ball spring-actuated lock. This lock has the advantages mentioned above. The round shape is similar to known portable cd-players and the pump is camouflaged when being used.

The breast pump according to the invention is easy to operate, allows the milk to be expressed even in confined areas with no set-down surfaces and, in addition, does not hinder the mother's mobility even as the milk is being expressed.

What is claimed is:

1. A portable breastpump, comprising:
   a motorized suction unit including a portable power source for the suction unit;
   a milk collecting unit having a breast shield within which a mother's breast is received for milk expression, a suction line connecting the collecting unit to the suction unit, and a milk-receiving container in fluid flow with the breast shield through a coupling element which rigidly but releasably unites the container to the collecting unit;
   a rigid housing enclosing the suction unit and power source, the housing having a front side and a back side which are in opposed relation and are connected with each other by a peripheral ball spring-actuated lock, the front side and the back side having a generally rounded smooth exterior around a circular circumference defining an area between the sides, the area smoothly extending into each of the front and back sides, the housing further having controls on its front side for operating the breastpump;
   a recess arranged in the circular circumference, wherein a first end of the suction line is adapted to be inserted into the recess in order to connect the suction unit to the collecting unit; and
   an attachment mechanism directly affixed to the housing which is attached to the mother's body, or suspended about the mother's body, so that the housing can be comfortably carried by the mother with the breastpump being exposed for use, the housing along with its enclosed suction unit and power source being hand-held in size and of a light weight to be comfortably carried;
   wherein the breastpump is portable during breastpumping.

2. The breastpump of claim 1 wherein the attachment mechanism is attached to the housing by a fastening means.

3. The breastpump of claim 2 wherein the fastening means comprises a clip.

4. The breastpump of claim 1 wherein the attachment mechanism is suspended about the mother's body by a tether.

5. The breastpump of claim 1 wherein the front side is dome-shaped.

6. A portable breastpump comprising:
   a motorized suction unit including a power source for the suction unit;
   a milk collecting unit having a breast shield within which a mother's breast is received for milk expression, a suction line connecting the collecting unit to the suction unit, and a milk-receiving container in fluid flow with the breast shield; and
   a housing enclosing the suction unit and power source, the housing being hand-held in size and having a front side and a rear side which are in opposed relation and are connected with each other by a peripheral ball spring-actuated lock, and a circular circumference connecting the front side and the rear side, whereby the front side, the rear side and the circular circumference define an oblate spheroid shape which has a short axis between the front and rear sides;
   the housing further comprising:
      controls arranged on the front side of the housing for operating the breastpump;
      a recess arranged in the circular circumference of the housing, wherein a first end of the suction line is adapted to be inserted into the recess in order to connect the suction unit to the collecting unit; and
      a resilient clip fixedly arranged on the rear side of the housing for fastening the housing on a carrying member, wherein the carrying member can be attached or applied on a mother's body;
   the breastpump being portable during breastpumping.

7. The breastpump of claim 6 wherein the housing comprises a second fastening mechanism for fastening the housing onto a second carrying member, wherein the second carrying member can be attached or applied on a mother's body.

8. The breastpump of claim 7 wherein the second fastening mechanism is releasable.

9. The breastpump of claim 7 wherein the second carrying member is suspended about the mother's body by a tether.

10. The breastpump of claim 6 wherein the front side is dome-shaped.

11. A portable breastpump, comprising:
    a motorized suction unit including a portable power source for the suction unit;
    a milk collecting unit having a breast shield within which a mother's breast is received for milk expression, a suction line connecting the collecting unit to the suction unit, and a milk-receiving container in fluid flow with the breast shield through a coupling element which rigidly but releasably unites the container to the collecting unit;
    a rigid housing enclosing the suction unit and power source, the housing having a front side and a back side which are in opposed relation and are connected with each other by a peripheral ball spring-actuated lock, the front side and the back side each having a generally rounded smooth exterior around a circular circumference defining an area between the sides, the area smoothly extending into each of the front and back sides, the housing further having controls on its front side for operating the breastpump, wherein the housing is hand-held in size;
    the housing further comprising:
       controls arranged on the front side of the housing for operating the breastpump;
       a recess arranged in the circular circumference of the housing, wherein a first end of the suction line is adapted to be inserted into the recess in order to connect the suction unit to the collecting unit; and
       a resilient clip fixedly arranged at the back side of the housing for fastening the housing on a carrying member, wherein the carrying member can be attached or applied on a mother's body;
    the breastpump being portable during breastpumping.

* * * * *